US011951246B1

(12) United States Patent
Kahn

(10) Patent No.: US 11,951,246 B1
(45) Date of Patent: Apr. 9, 2024

(54) SYSTEMS AND METHODS FOR COACHING INHALER USE VIA SYNCHRONIZING PATIENT AND RESPIRATORY CYCLE BEHAVIORS

(71) Applicant: Yale University, New Haven, CT (US)

(72) Inventor: Peter Kahn, New Haven, CT (US)

(73) Assignee: Yale University, New Haven, CT (US)

( * ) Notice: Subject to any disclaimer, the term of this patent is extended or adjusted under 35 U.S.C. 154(b) by 0 days.

(21) Appl. No.: 18/373,558

(22) Filed: Sep. 27, 2023

(51) Int. Cl.
*A61M 15/00* (2006.01)
*A99Z 99/00* (2006.01)
*G16H 20/13* (2018.01)
*G16H 40/63* (2018.01)

(52) U.S. Cl.
CPC ......... *A61M 15/0001* (2014.02); *A99Z 99/00* (2019.05); *G16H 20/13* (2018.01); *G16H 40/63* (2018.01); *A61M 2205/52* (2013.01); *A61M 2205/581* (2013.01); *A61M 2205/582* (2013.01); *A61M 2205/583* (2013.01); *A61M 2230/42* (2013.01)

(58) Field of Classification Search
None
See application file for complete search history.

(56) References Cited

U.S. PATENT DOCUMENTS

| | | | | |
|---|---|---|---|---|
| 2016/0129182 A1* | 5/2016 | Schuster | ............. | A61M 15/008 702/56 |
| 2016/0166766 A1* | 6/2016 | Schuster | ................. | G01F 22/00 702/54 |
| 2022/0115107 A1* | 4/2022 | Gondalia | ............... | G16H 10/20 |

FOREIGN PATENT DOCUMENTS

| WO | WO-2021038467 A1 * | 3/2021 | ........... A61B 5/0876 |
|---|---|---|---|
| WO | WO-2022261125 A1 * | 12/2022 | ........... A61B 5/0876 |

OTHER PUBLICATIONS

Dhanan et al.; Fundamentals of aerosol therapy in critical care; Critical Care (2016) 20:269; pp. 1-16.
Kocks et al.; Identifying critical inhalation technique errors in Dry Powder Inhaler use in patients with COPD based on the association with health status and exacerbations: findings from the multi-country cross-sectional observational PIFotal study; BMC Pulmonary Medicine (2023) 23:302; pp. 1-16.
Leiner et al; Inhalation Devices and Patient Interface: Human Factors; The AAPS Journal, vol. 17, No. 2, Mar. 2015 (# 2015); pp. 457-461.

(Continued)

*Primary Examiner* — Manuel A Mendez
(74) *Attorney, Agent, or Firm* — Murtha Cullina LLP; Anthony P. Gangemi

(57) ABSTRACT

A method of coaching a patient to use an inhaler for medication delivery is provided. The method includes obtaining, via a sensor, respiratory behavior data of the patient; receiving, at a computing device, the respiratory behavior data; performing a respiratory pattern analysis algorithm on the respiratory behavior data to determine a desired interval of inhaler actuation for medication delivery; communicating a cue signal to actuate the inhaler to achieve the desired interval; obtaining, via the sensor, inhaler actuation data based on the actuation of the inhaler; receiving, at the computing device, the inhaler actuation data; performing an actuation analysis algorithm on the inhaler actuation data to assess the efficacy of the actuation; and adjusting the cue signal to actuate the inhaler to improve the efficacy of a future actuation.

20 Claims, 5 Drawing Sheets

(56) References Cited

OTHER PUBLICATIONS

Trainhaler CR Technical specifications; Clement Clarke International Ltd; Part No. 3152202 issue Mar. 2, 2021; pp. 1-2.
Mekonnen, et al; A review of upper airway physiology relevant to the delivery and deposition of inhalation aerosols; pp. 1-15.
De Vries, et al; Pulmonary Disease Aerosol Delivery Devices A guide for physicians, nurses, pharmacists, and other health care professionals 4th Edition; Produced in collaboration with the American Association for Respiratory Care; 2023; pp. 1-71.
Rangaraj, et al.; Insight into pulmonary drug delivery: Mechanism of drug deposition to; device characterization and regulatory requirements; Department of Pharmaceutics, National Institute of Pharmaceutical Education and Research (NIPER-HYD), Balanagar, Telangana, 500037, India; Pulmonary Pharmacology & Therapeutics 54 (2019) pp. 1-21.
Bosnic-Anticevich, et al.; Recognizing and Tackling Inhaler Technique Decay in Asthma and Chronic Obstructive Pulmonary Disesase (COPD) Clinical Practice; J Allergy Clin Immunol Pract Month 2023; pp. 1-15.
Supplementary material; to Identifying critical inhalation technique errors; 2023; pp. 1-5.
Rospond1, et al; The history, current state and perspectives of aerosol therapy; Acta Pharm. 72 (2022) 225-243.

* cited by examiner

SYSTEMS AND METHODS FOR COACHING INHALER USE VIA SYNCHRONIZING PATIENT AND RESPIRATORY CYCLE BEHAVIORS

FIELD

The present technology relates generally to the field of pulmonary medicine delivery and more particularly, to systems and methods for training the correct use of inhalers.

BACKGROUND

Currently, a large number of medications used in the field of pulmonary medicine are delivered via the inhalational route. The use of inhalation facilitates the direct delivery of an active pharmaceutical compound to the end organ of interest (i.e., the lungs), thus maximizing on-target effects for a given dose of medication and minimizing off-target effects. Definitionally, the use of inhaled medications requires the need for appropriate delivery mechanisms. These delivery mechanisms can introduce uncertainty and human factors deviations from suggested desired use protocols. Unlike pills, liquid, or other forms of medications which are simply swallowed or injected after which time the active pharmaceutical ingredient ("API") becomes available for therapeutic activity, inhaled therapeutics rely on the patient to inhale the API correctly using both appropriate technique and quantity of the delivered medication for this medication to have its desired effect.

To date, there have been two main modalities of drug delivery for inhalational use: the nebulizer and inhaler. While the nebulizer is an appealing way to deliver medication as it requires only passive tidal breathing on the part of the patient, nebulized medications take significantly longer time to deliver, may expose the user and surrounding personnel to the API, may result in imprecise dosing of medication, and is not able to accommodate all types of APIs as some may not be able to be formulated for nebulization. Additionally, not all nebulizers are portable, and they require careful cleaning after use. Unlike nebulizers, inhalers deliver a known quantity of medication in each actuation, are portable, can deliver combination therapies and can do so in a time efficient manner.

Unfortunately, given that the inhaler is a medical device, its proper use is not always guaranteed, thus impacting the delivery of the desired therapeutic. A higher number of inhaler use errors have been shown to lead to worse outcomes for chronic obstructive pulmonary disease ("COPD") patients. The most significant complication most frequently encountered in the world of pulmonary medicine is the lack of a patient's ability to readily understand and appropriately deploy the inhaler with consistent technique. This is exacerbated by the multiple different types of inhalers marketed. Although a medication may be most appropriate for a patient, therapeutic benefit may not be achieved due to human factors challenges, most prominently the lack of a patient's ability to coordinate their inhalation with the simultaneous deployment of an actuation from an inhaler.

As a result of these challenges healthcare providers have worked to design inhaler teaching programs to ensure that patients are properly educated on how to deploy respiratory medications via an inhaler both during the initial phase of use and in maintenance phases thereafter. Other solutions such as a spacer have been developed in an effort to deliver medication when patients are unable to synchronously breathe in with the deployment of an inhaler, the use of placebo inhalers to propose appropriately timed inhalation, audio-based teaching devices, and digital videos and other teaching-based modalities to support patient learning.

While these solutions are helpful for some patients, not all medications can be used with a spacer and not all patients are able to effectively coordinate their inhalation with all inhaler types even with repeated prompting or teaching. Additionally, not all inhaler types can be used by all patient types due to mismatches in patient abilities to generate appropriate flow for each inhaler or the lack of a medication being prepared in the desired formulation. As used herein and unless indicated otherwise, the term "inhaler" encompasses all types of medical devices used for delivering medicines into the lungs through the work of a person's breathing that require actuation by the patient to administer a dose of medication. The term "inhaler" thus excludes nebulizers. Metered-dose, dry powder, and soft mist inhalers are examples of inhalers contemplated for use with the present technology.

What is needed, therefore, is an improved system and method for training the correct use of inhalers that addresses at least some of the problems described above.

SUMMARY

According to an embodiment of the present technology, a method of coaching a patient to use an inhaler for medication delivery is provided. The method includes obtaining, via a sensor, respiratory behavior data of the patient; receiving, at a computing device, the respiratory behavior data; performing a respiratory pattern analysis algorithm on the respiratory behavior data to determine a desired interval of inhaler actuation for medication delivery; communicating a cue signal to actuate the inhaler to achieve the desired interval of inhaler actuation; obtaining, via the sensor, inhaler actuation data based on the actuation of the inhaler; receiving, at the computing device, the inhaler actuation data; performing an actuation analysis algorithm on the inhaler actuation data to assess the efficacy of the actuation; and adjusting, if the efficacy of the actuation is below a predetermined threshold, the cue signal to actuate the inhaler to improve the efficacy of a future actuation.

In some embodiments, performing the respiratory pattern analysis algorithm includes analyzing the respiratory behavior data to determine a current breathing pattern of the patient; confirming that the current breathing pattern is predictable within a predetermined margin of error; confirming that the current breathing pattern is compatible with medication delivery via actuation of the inhaler; and synchronizing the current breathing pattern with the actuation of the inhaler to determine the desired interval of inhaler actuation.

In some embodiments, confirming that the current breathing pattern is predictable within a predetermined margin of error includes measuring the integral of flow over time for a predetermined number of breaths by the patient, performing signal processing algorithms, performing machine learning models, performing statistical analysis, performing biofeedback training, performing anomaly detection algorithms, performing data normalization via integration with additional physiological data of the patient, performing deep learning models, performing ensemble models, performing adaptive algorithms, or combinations thereof.

In some embodiments, confirming that the current breathing pattern is compatible with medication delivery via actuation of the inhaler includes cross-referencing the current breathing pattern with an inhaler characteristics database, performing respiratory pattern matching, performing inhalation profile analysis, monitoring the flow rate of the current breathing pattern, performing adaptive algorithms, combining respiratory behavior data obtained from a plurality of sensors, analyzing patient feedback, performing clinical outcome monitoring, performing artificial intelligence enhanced prediction models, performing data augmentation, or combinations thereof.

In some embodiments, synchronizing the current breathing pattern with the actuation of the inhaler to determine the desired interval of inhaler actuation includes performing inhalation phase detection, performing desired flow rate identification, performing volume-based actuation, performing artificial intelligence enhanced prediction models, and analyzing preferences of the patient.

In some embodiments, the method further includes communicating a sample cue signal to the patient to perform a pseudo actuation of the inhaler; obtaining, via the sensor, sample inhalation data of the patient; receiving, at the computing device, the sample inhalation data; and performing the respiratory pattern analysis algorithm on the sample inhalation data.

In some embodiments, performing the actuation analysis algorithm includes determining if the inhaler was actuated at the desired interval; creating an actuation instance data log based, at least in part, on the inhaler actuation data; communicating the actuation instance data log to a database; correlating the actuation instance data log with historical data of the patient and historical data of similarly diagnosed patients stored on the database to track and monitor symptoms, side-effects, and exacerbations of a pathological condition of the patient being treated by the inhaler-delivered medication; determining the efficacy of the actuation based, at least in part, on the correlated actuation instance data log; and developing an adjusted cue signal to improve the efficacy of a future actuation.

In some embodiments, performing the actuation analysis algorithm further includes analyzing the environmental impact of the inhaler; and determining whether an alternative inhaler having a more beneficial environmental impact than the environmental impact of the inhaler is available for use with the patient's medication.

In some embodiments, performing the actuation analysis algorithm includes performing continuous respiratory monitoring, performing medication adherence tracking, analyzing patient feedback, reporting the inhaler actuation data to the patient and the patient's healthcare provider, or combinations thereof.

In some embodiments, the cue signal is communicated to the patient and the cue signal comprises an audio cue, a visual due, a haptic cue, or combinations thereof.

In some embodiments, the cue signal is communicated to an actuation mechanism of the inhaler that is configured to automatically actuate the inhaler upon receiving the cue signal.

According to another embodiment of the present technology, a system for coaching a patient to use an inhaler for medication delivery is provided. The system includes an inhaler configured for medication delivery, a patient prescribed to use the inhaler for medication delivery, a sensor configured to obtain respiratory behavior data of the patient; and a computing device configured to receive the respiratory behavior data. The computing device includes inhaler coaching circuitry and a memory configured to execute instructions of the inhaler coaching circuitry via at least one processor. The instructions include steps for obtaining, via the sensor, respiratory behavior data of the patient; receiving, at the computing device, the respiratory behavior data; performing a respiratory pattern analysis algorithm on the respiratory behavior data to determine a desired interval of inhaler actuation for medication delivery; communicating a cue signal to actuate the inhaler to achieve the desired interval of inhaler actuation; obtaining, via the sensor, inhaler actuation data based on the actuation of the inhaler; receiving, at the computing device, the inhaler actuation data; performing an actuation analysis algorithm on the inhaler actuation data to assess the efficacy of the actuation; and adjusting, if the efficacy of the actuation is below a predetermined threshold, the cue signal to actuate the inhaler to improve the efficacy of a future actuation.

According to yet another embodiment of the present technology, a non-transitory computer readable medium is provided. The non-transitory computer readable medium includes instructions that, when executed by at least one processor, coach a patient to use an inhaler for medication delivery. The instructions include the steps of obtaining, via a sensor, respiratory behavior data of the patient; receiving, at a computing device, the respiratory behavior data; performing a respiratory pattern analysis algorithm on the respiratory behavior data to determine a desired interval of inhaler actuation for medication delivery; communicating a cue signal to actuate the inhaler to achieve the desired interval; obtaining, via the sensor, inhaler actuation data based on the actuation of the inhaler; receiving, at the computing device, the inhaler actuation data; performing an actuation analysis algorithm on the inhaler actuation data to assess the efficacy of the actuation; and adjusting, if the efficacy of the actuation is below a predetermined threshold, the cue signal to actuate the inhaler to improve the efficacy of a future actuation.

Further objects, aspects, features, and embodiments of the present technology will be apparent from the drawing Figures and below description.

BRIEF DESCRIPTION OF DRAWINGS

Some embodiments of the present technology are illustrated as an example and are not limited by the figures of the accompanying drawings, in which like references may indicate similar elements.

DETAILED DESCRIPTION

Accordingly, embodiments of the present technology are directed to systems, non-transitory computer-readable media, and methods for coaching a patient how to correctly use an inhaler for medicine delivery. In some embodiments, digital coaching software is used in combination with respiratory monitoring technology to ensure that the patient can observe their own respiratory cycle and deploy inhaled medications at the appropriate time in their respiratory cycle with coaching from the software. After connecting to a respiratory monitor, a patient or the software observes the patient's breathing to develop a pattern that is learned by the software. After the required number of breaths to develop this pattern, the software then coaches the patient on precisely when to deploy their inhaler in conjunction with expiration and inspiration so as to maximize the chance of success with each dose of the medication. In some embodiments, the software communicates an electronic cue signal to an actuation mechanism of the inhaler to automatically actuate the inhaler and deliver the dose of the medication at the appropriate time.

Figure 1:
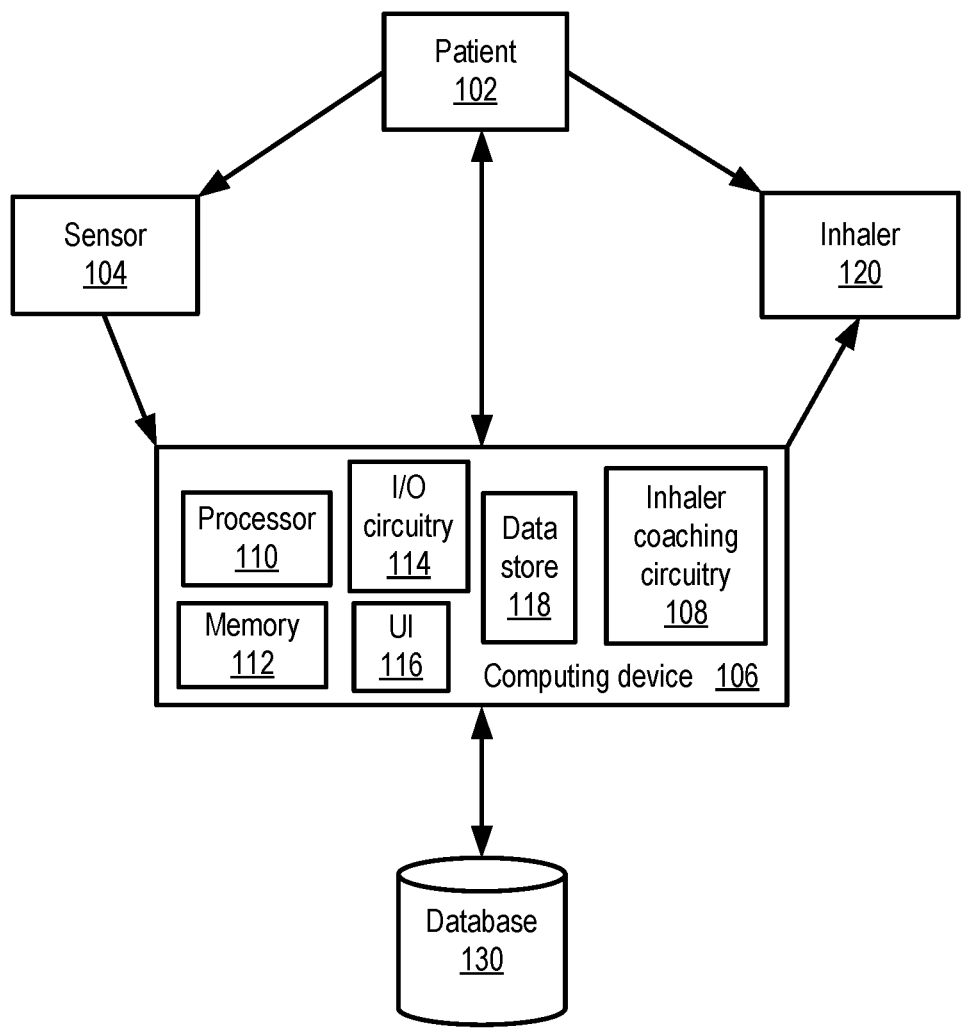
FIG. 1 is a functional block diagram of a system for coaching a patient to use an inhaler for medication delivery according to some embodiments of the present technology.

FIG. 1 illustrates a functional block diagram of an inhaler coaching system 100 according to some embodiments of the present technology. Inhaler coaching system 100 works with a patient 102 who has been prescribed a medication delivery via an inhaler 120. A sensor 104 is configured to obtain respiratory behavior data of the patient 102 and to communicate the respiratory behavior data to a computing device 106. The sensor 104 may include invasive or non-invasive monitoring of the patient 102 via any combination of the types of sensors discussed in more detail below regarding inhaler coaching method 200 of FIG. 2.

Computing device 106 may include, but is not limited to, a computing system (e.g., a server, a workstation computer, a desktop computer, a laptop computer, a tablet computer, an ultraportable computer, an ultramobile computer, a netbook computer and/or a subnotebook computer, etc.) and/or a Smartphone. Computing device 106 includes a processor 110, a memory 112, input/output ("I/O") circuitry 114, a user interface ("UI") 116, data store 118, and inhaler coaching circuitry 108.

Processor 110 is configured to control overall operations of the computing device 106 and its associated components, such as inhaler coaching circuitry 108 which includes the algorithms discussed in more detail below regarding inhaler coaching method 200 of FIG. 2. Memory 112 may be configured to store data associated with inhaler coaching circuitry 108. I/O circuitry 114 may be configured to provide wired and/or wireless communication functionality for inhaler coaching circuitry 108. For example, I/O circuitry 114 may be configured to receive respiratory behavior data from the sensor 102, provide inhaler actuation cues to the patient 102 after processing and analysis of the respiratory behavior data by inhaler coaching circuitry 108, and receive user feedback from the patient 102. In another example, I/O circuitry 114 may be configured to receive inhaler characteristics data, historical user data (of the patient 102 and/or other similarly matched users), environmental initiative data, etc. from database 130, as discussed in more detail below regarding inhaler coaching method 200 of FIG. 2. UI 116 may include a user input device (e.g., keyboard, mouse, microphone, touch sensitive display, etc.) and/or a user output device, e.g., a display. Data store 118 may be configured to store one or more of respiratory behavior data, inhaler requirement data, inhaler characteristics data, historical user data, environmental initiative data, etc.

Figure 2:
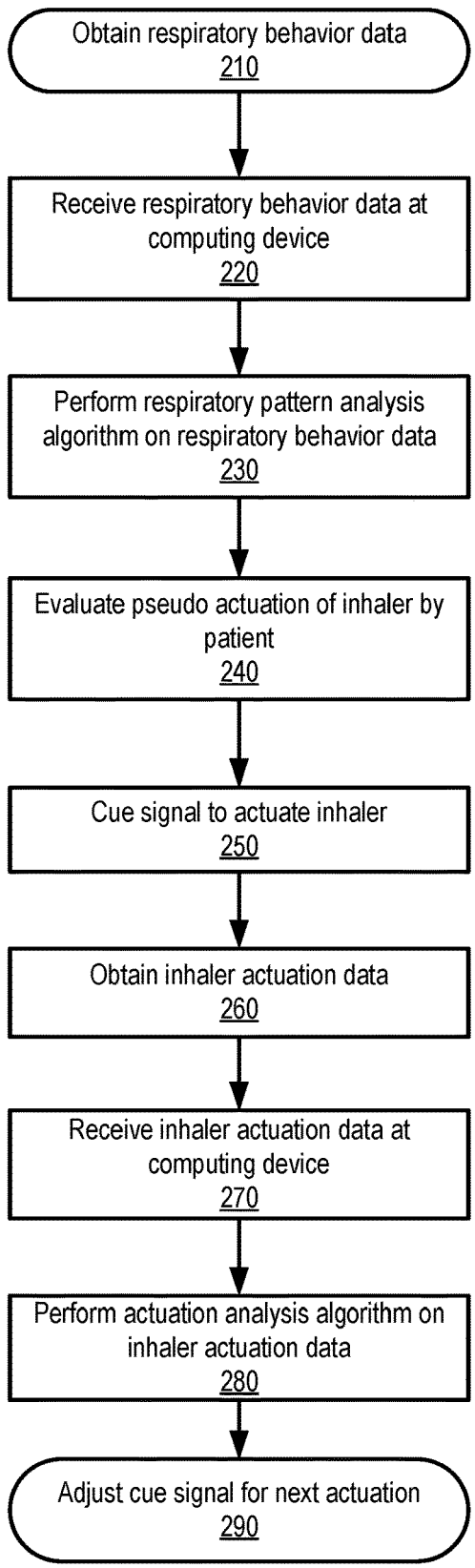
FIG. 2 is a flowchart of a method of coaching a patient to use an inhaler for medication delivery according to some embodiments of the present technology.

FIG. 2 illustrates a flowchart of an inhaler coaching method 200 according to some embodiments of the present technology. At 210, the method 200 includes obtaining, via the sensor 104, respiratory behavior data of the patient 102. The sensor includes any respiratory monitoring technology for measuring breathing that outputs an electronic signal indicative of one or more characteristics of a patient's breathing. In one embodiment, the sensor is a flow sensor that measures flow rate and volume. In other embodiments, the sensor includes invasive monitoring, non-invasive monitoring, skin monitoring, mouth and/or nose monitoring, cardiac activity monitoring, neural activity monitoring, etc., or combinations thereof. For example, in some embodiments, the sensor includes chest straps and bands that fit around the patient's chest or abdomen and measure the expansion and contraction during breathing. The chest straps and bands include digital or analog strain gauges to detect movement. The chest straps and bands can be wired or wireless. In some embodiments, the sensor includes wearable devices (e.g., Smartwatches, Fitness Trackers, etc.) that are configured to estimate respiration rates through motion detection, ballistocardiography, or photoplethysmography. In some embodiments, the sensor includes spirometers that measure the volume of air inspired and expired by the patient's lungs via pressure, flow, and/or oscillometry methods. In some embodiments, the sensor includes microphone-based systems wherein a microphone (e.g., a dedicated microphone, a microphone that is part of a Smartphone or Smart Speaker, etc.) is placed near the patient's mouth or nose to detect breath sounds. In some embodiments, the sensor includes thermal sensors placed under the patient's nose to detect the change in temperature between inhaled and exhaled air. In some embodiments, the sensor includes impedance pneumography to measure changes in electrical impedance between two electrodes places on the patient's chest to estimate respiratory activity. In some embodiments, the sensor includes capnography devices (e.g., portable or stationary) to measure the concentration of carbon dioxide in exhaled air to provide data on respiratory rate and depth. In some embodiments, the sensor includes camera-based monitoring wherein a camera (e.g., a dedicated camera, a camera that is part of a Smartphone, etc.) captures the patient's chest movements and uses image processing algorithms to calculate the respiratory rate. In some embodiments, the sensor includes radar-based or radio wave systems that use radar or radio waves to detect body movements associated with breathing. These systems may include standalone devices or be integrated into larger systems such as Smart Home Networks. In some embodiments, the sensor includes bio-impedance measurement methods that estimate lung volume by measuring the resistance of the patient's body to small amount of electric current. In some embodiments, the sensor includes any combination of the respiratory monitoring technologies discussed above.

At 220 the method 200 includes receiving, at the computing device 106, the respiratory behavior data obtained by the sensor. Inhaler coaching circuitry 108 of the computing device 106 is configured to execute the automated processes discussed herein to analyze the patient's breathing pattern, generate cues for training the patient how to correctly use the inhaler, monitor the patient's use of the inhaler after receiving the training cues, and adjusting the training cues based on how efficiently the patient uses the inhaler. The processor 110 and inhaler coaching circuitry 108, and their associated components, enable the computing device 106 to perform a series of computer-readable instructions to execute the automated processes discussed herein.

At 230 the method 200 includes performing a respiratory pattern analysis algorithm on the respiratory behavior data to determine a desired interval of inhaler actuation. In some embodiments, the desired interval of inhaler actuation is in the range of about 0.5 seconds to about 1.5 seconds after the patient's inhalation phase begins. In some embodiments, the desired interval of inhaler actuation is about 1 second after the patient's inhalation phase begins. However, the present technology is not limited thereto and contemplates embodiments where the desired interval of inhaler actuation occurs at various time instances and intervals after the patient's inhalation phase begins, such as 0.5 seconds, 1.5 seconds, about 2 seconds, in the range of about 0.5 seconds to about 1 second, in the range of about 1 second to about 1.5 seconds, in the range of about 1 second to about 2 seconds, etc.

Figure 3:
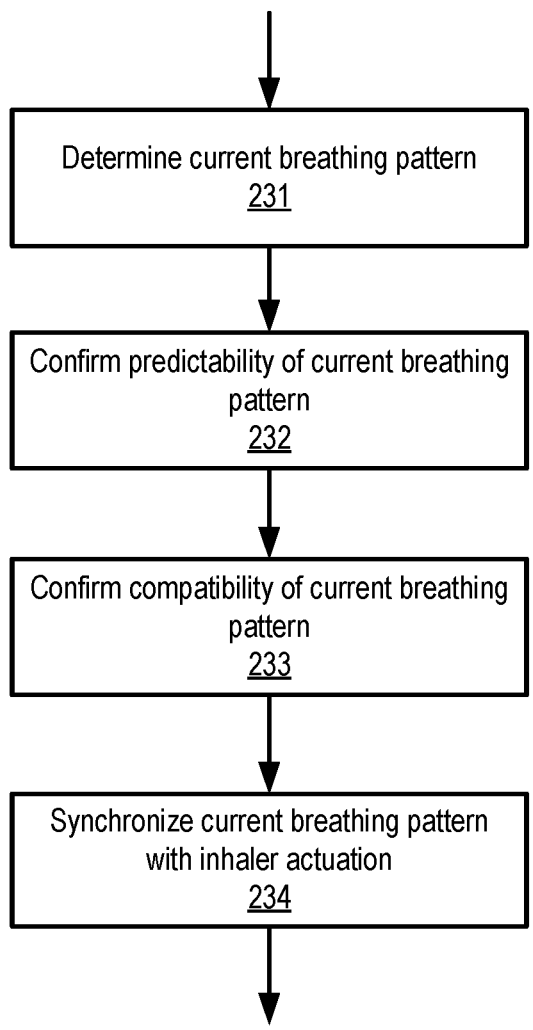
FIG. 3 is a flowchart further outlining the respiratory pattern analysis algorithm of the method of FIG. 2.

FIG. 3 illustrates a flowchart of the step 230 of performing the respiratory pattern analysis algorithm according to some embodiments of the present technology. At 231, the respiratory pattern analysis algorithm includes analyzing the respiratory behavior data to determine the current breathing pattern of the patient and to confirm that the current breathing pattern is predictable within a predetermined margin of error. In some embodiments, the respiratory pattern analysis algorithm determines the current breathing pattern by measuring the integral of flow over time (i.e., the mathematical integral of the volume of air measured by the sensor during inhalation and exhalation for a single breath) for three breaths and comparing the integral of flow across the three breaths. In some embodiments, if the integral of flow is within about 10% for each breath, then the current breathing pattern is confirmed as predictable. In some embodiments, the respiratory pattern analysis algorithm determines the current breathing pattern by measuring the total tidal volume for three breaths (i.e., the sensor measures the total volume of air inhaled and exhaled for each breath) and ensuring that there is about 10% or less error over the three breaths. However, the present technology is not limited in this regard and contemplates embodiments that measure the integral of flow and/or the total tidal volume over any number of breaths (e.g., 2, 4, 5, 6, etc.) and that use different predetermined margins of error (e.g., the integral of flow and/or the total tidal volume being within about 5%, 15%, in the range of about 5% to about 15%, etc., for each breath).

At 232, the respiratory pattern analysis algorithm confirms that the current breathing pattern is predictable within the predetermined margin of error by additional and/or alternative means. For example, in some embodiments, the respiratory pattern analysis algorithm includes signal processing algorithms that use filtering techniques such as Fourier transforms, wavelet transforms, or digital filtering. In some embodiments, the respiratory pattern analysis algorithm includes machine learning models that use advanced algorithms such as recurrent neural networks ("RNNs") or long short-term memory ("LSTM") networks to predict future respiratory patterns based on past data from the patient and, in some embodiments, a broader set of data from similarly matched users. In some embodiments, the respiratory pattern analysis algorithm includes statistical analysis techniques such as autocorrelation or spectral density estimation to measure the predictability of the patient's respiratory cycle and, in some embodiments, measure entropy (e.g., sample entropy, approximate entropy, cross entropy, multi-scale entropy). In some embodiments, the respiratory pattern analysis algorithm includes biofeedback training wherein visual, auditory, and/or haptic feedback is provided to guide the patient to regulate their breathing to generate predictable breathing pattern. In some embodiments, the respiratory pattern analysis algorithm includes anomaly detection algorithms that are configured to exclude abnormal breaths from the pattern recognition process. In some embodiments, the respiratory pattern analysis algorithm includes data normalization via integration with other physiological data such as heart rate or body temperature to enhance the predictability of the respiratory cycle through artificial intelligence ("AI") and methods of multivariate analyses. In some embodiments, the respiratory pattern analysis algorithm includes deep learning models such as convolutional neural networks ("CNNs") to recognize complex patterns in the patient's respiratory cycle. In some embodiments, the respiratory pattern analysis algorithm includes ensemble models that combine a plurality of prediction models that each predict different aspects of the patient's respiratory cycle to create a more robust and accurate overall prediction model. In some embodiments, the respiratory pattern analysis algorithm includes adaptive algorithms that adjust their behavior based on the patient's respiratory behavior data that they are processing. In some embodiments, the respiratory pattern analysis algorithm includes any combination of the breath pattern prediction methods discussed above.

At 233, the respiratory pattern analysis algorithm includes confirming that the current breathing pattern is compatible with medication delivery via actuation of the inhaler. In some embodiments, the respiratory pattern analysis algorithm confirms the compatibility of the current breathing pattern by determining if the flow rate of the current breathing pattern is in the range of about 20 L/min to about 90 L/min. In some embodiments, the current breathing pattern is compatible if the average flow rate of the current breathing pattern is in the range of about 20 L/min to about 90 L/min. In some embodiments, the current breathing pattern is compatible if a minimum flow rate for any breath of the pattern is about 20 L/min and a maximum flow rate for any breath of the pattern is about 90 L/min. The flow rate of the current breathing pattern can be obtained directly from the respiratory behavior data measured by the sensor 104 or calculated by the respiratory pattern analysis algorithm from the respiratory behavior data. For example, in embodiments where the sensor 104 measures respiratory behavior data as a unit of pressure (e.g., psi, bar, etc.) and the respiratory pattern analysis algorithm calculates the flow rate therefrom.

In some embodiments, the system includes an inhaler characteristics database that is accessed by the respiratory pattern analysis algorithm. The inhaler characteristics database includes data on various inhaler types, each with their specific requirements for desired medication delivery. These requirements can include inhalation speed, volume, flow rate, and breath-holding duration. The system is configured to match the patient's inhaler to its corresponding entry in the database to extract the inhaler's specific requirements.

In some embodiments, the respiratory pattern analysis algorithm includes respiratory pattern matching wherein the system cross-references the patient's established respiratory pattern with the inhaler's requirements to ensure that the patient's breath pattern, such as inhalation speed and volume, aligns with the inhaler's requirements for desired medication delivery and/or is similarly matched with the patient's prior breath patterns or breath patterns of other users that have had successful clinical outcomes with the same inhaler.

In some embodiments, the respiratory pattern analysis algorithm includes inhalation profile analysis wherein the system analyzes the patient's inhalation profile, including inhalation speed, volume, and depth, to ensure it is compatible with the inhaler's requirements. In some embodiments, if the patient's inhalation profile does not meet the inhaler's requirements, the system provides feedback and coaching to help the patient adjust their inhalation technique or recommend an alternative inhaler or therapeutic option. Different inhalers require different flow rates to deliver the API. In some embodiments, the respiratory pattern analysis algorithm is informed of what type of inhaler is being used by the patient and thus measures the flow rates generated by the patient in real-time to ensure that the flow rates are sufficient for the given type of medication. If the flow rates are sufficient, then the medication delivery proceeds as planned via the method steps discussed herein. If the flow rates are insufficient, then the system recommends a more appropriate type of delivery device to match the patient's needs and ability to generate flow rates.

In some embodiments, the respiratory pattern analysis algorithm includes flow rate monitoring wherein the system monitors the patient's flow rate during inhalation and compares it to the inhaler's requirements. Some inhalers, such as dry powder inhalers ("DPIs"), require a specific flow rate for desired medication delivery. If the patient's flow rate is too low or too high, the system provides feedback and coaching to help the patient adjust their inhalation technique. For example, in some embodiments the respiratory pattern analysis algorithm determines if the flow rate is in the range of about 20 L/min to about 90 L/min and instructs the system to provide feedback and coaching to the patient if the flow rate is outside this range.

In some embodiments, the respiratory pattern analysis algorithm includes adaptive algorithms that are configured to adjust the timing of inhaler cues based on the patient's changing respiratory patterns. If the patient's breathing becomes irregular or if the inhalation profile does not meet the inhaler's requirements, the system is configured to delay or modify the cues until the patient's breathing stabilizes.

In some embodiments, the respiratory pattern analysis algorithm includes sensor fusion wherein the system includes additional sensors, such as flow sensors or pressure sensors, to provide a more comprehensive view of the patient's breath pattern. By combining data from multiple sensors, the system is configured to more accurately assess whether the patient's breath pattern is sufficient for medication delivery.

In some embodiments, the respiratory pattern analysis algorithm includes user feedback wherein the system permits the patient to provide feedback on the effectiveness of the medication delivery. The respiratory pattern analysis algorithm is configured to use this feedback to improve its accuracy in assessing the sufficiency of the respiratory pattern. For example, if the patient rates their perceived efficacy, the system can then aim to adjust itself to achieve a higher patient score based on a predetermined targeted end point.

In some embodiments, the respiratory pattern analysis algorithm includes clinical outcome monitoring wherein the system monitors (via e.g., the various sensors discussed herein, user feedback, etc.) clinical outcomes, such as symptom relief or lung function improvements, to assess the effectiveness of the medication delivery. If the patient does not experience the expected benefits, the system is configured to adjust the respiratory pattern analysis algorithm or recommend a different inhaler type.

In some embodiments, the respiratory pattern analysis algorithm includes AI-enhanced prediction models that are configured to predict the patient's future breath patterns based on historical data. In some embodiments, the respiratory pattern analysis algorithm includes data augmentation techniques that are configured to generate synthetic respiratory patterns based on the patient's actual respiratory pattern data. In some embodiments, the respiratory pattern analysis algorithm includes any combination of the breath pattern compatibility confirmation methods discussed above.

At 234, the respiratory pattern analysis algorithm includes synchronizing the current breath pattern with the actuation of the inhaler to determine the desired interval of inhaler actuation. The respiratory pattern analysis algorithm is configured to synchronize the patient's current tidal breath inspiration with the medication delivery such that the patient can precisely time actuation of the inhaler to receive an effective dose of the medication. For example, in some embodiments, the respiratory pattern analysis algorithm includes inhalation phase detection to identify the onset of the inhalation phase of the patient's respiratory cycle and then electronically cue the patient (or send an electronic actuation signal to an actuation mechanism of the inhaler) to trigger the inhaler to actuate at the start of this phase. In some embodiments, the respiratory pattern analysis algorithm cues for inhaler actuation about 1 second after the inhalation phase begins. In some embodiments, the respiratory pattern analysis algorithm cues for inhaler actuation in the range of about 0.5 seconds to about 1.5 seconds after the inhalation phase begins. However, the present technology is not limited thereto and contemplates embodiments where the respiratory pattern analysis algorithm cues for inhaler actuation at different times after the inhalation phase begins, such as 0.5 seconds, 1.5 seconds, about 2 seconds, in the range of about 0.5 seconds to about 1 second, in the range of about 1 second to about 1.5 seconds, in the range of about 1 second to about 2 seconds, etc.

In some embodiments, the respiratory pattern analysis algorithm includes desired flow rate identification that is configured to analyze the patient's inhalation flow rate and determine the desired interval for inhaler actuation. This is particularly useful for DPIs, which require a specific flow rate for desired medication dispersion. The algorithm monitors the patient's flow rate in real-time and cues the patient or an actuation mechanism of the inhaler (e.g., remove a barrier to inhaler flow, close a bypass door, etc.) to actuate when the flow rate reaches the desired value. In some embodiments, the desired value is determined by the algorithm measuring the duration of inhalation and determining the point of greatest flow of inhalation, at which point actuation of the inhaler is triggered (e.g., by cueing the patient or automatically by signaling the actuation mechanism of the inhaler).

In some embodiments, the respiratory pattern analysis algorithm includes volume-based actuation that is configured to monitor the patient's inhalation volume and trigger the inhaler when a specific volume threshold (e.g., determined via the inhaler's specific requirements) is reached. In some embodiments, the respiratory pattern analysis algorithm includes inhalation patterns wherein the algorithm analyzes historical data (e.g., the patient's past respiratory pattern data) to predict the timing and characteristics of the patient's next inhalation and actuates the inhaler at the desired interval (e.g., determined via the inhaler's specific requirements).

In some embodiments, the respiratory pattern analysis algorithm includes AI-enhanced prediction models, such as RNNs and LSTM networks, to predict the patient's inhalation patterns. In some embodiments, the respiratory pattern analysis algorithm includes user preferences wherein the patient is permitted to customize the timing of inhaler actuation based on their preferences. For example, the patient may customize the timing of inhaler actuation to occur automatically 1 second after their inhalation phase begins. In some embodiments, the respiratory pattern analysis algorithm includes any combination of the current breath pattern synchronization methods discussed above.

Figure 4:
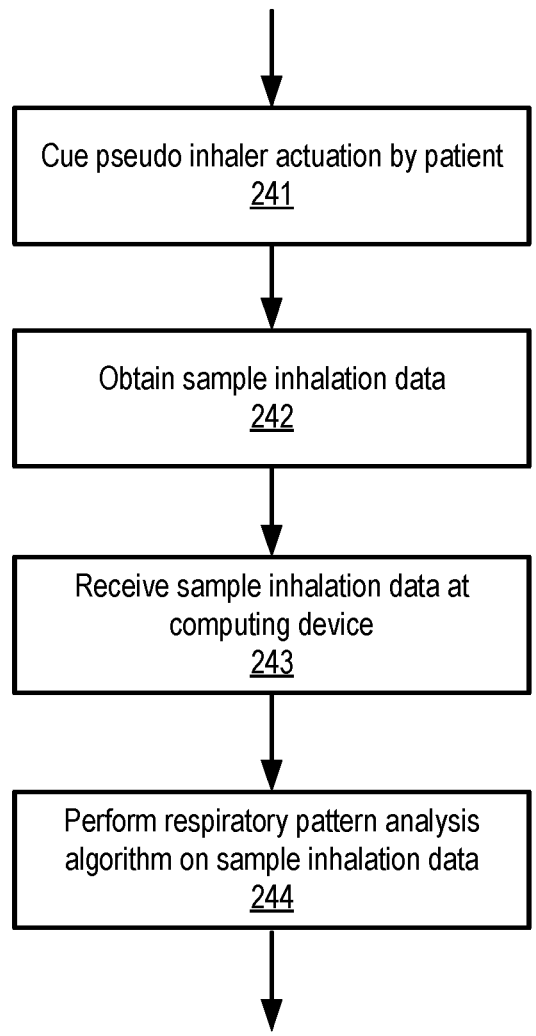
FIG. 4 is a flowchart further outlining the pseudo inhaler actuation evaluation step of the method of FIG. 2.

In some embodiments, at 240 the method 200 includes evaluating a pseudo actuation of the inhaler by the patient. FIG. 4 illustrates a flowchart of the step 240 of evaluating a pseudo actuation of the inhaler according to some embodiments of the present technology. At 241, the system communicates a sample cue signal to the patient to perform a pseudo actuation of the inhaler. At 242, sample inhalation data of the patient is obtained by the sensor as the patient performs the pseudo actuation. At 243, the sample inhalation data is received at the computing device. At 244, the system performs the respiratory pattern analysis algorithm described above on the sample inhalation data. For example, in some embodiments the system cues the patient to perform a sample inhalation on the inhaler as if they intended to inhale while actuating the inhaler. As the patient performs the sample inhalation, the system receives sample inhalation data from the sensor and instructs the above-described algorithms to perform any combination of the above-described analyses as if the patient were actuating their inhaler, thereby performing a quality control step.

The sample inhalation provides additional benefits such as training and coaching, calibration, and personalization. Regarding training and coaching, a sample inhalation allows the patient to practice their inhalation technique under the guidance of the system. The system can provide real-time feedback on the patient's inhalation technique, such as inhalation speed, volume, and depth. This training can help the patient improve their technique and better ensure improved medication delivery during the actual inhalation. Regarding calibration, a sample inhalation can be used to calibrate the system's algorithms. By analyzing the patient's inhalation patterns during the sample inhalation, the system can adjust its algorithms to predict the patient's future inhalation patterns more accurately. In some embodiments, the system includes a calibration device to ensure that the sensor continuously functions as desired. Regarding personalization, a sample inhalation allows the system to personalize its algorithms to the patient's unique breathing patterns. During the sample inhalation, the system can determine whether the patient's breathing technique meets the inhaler's requirements for desired medication delivery. If the patient's breathing technique does not meet the inhaler's requirements, the system can provide feedback and coaching to help the patient adjust their breathing technique or recommend a different inhaler type.

At 250, the method 200 includes communicating a cue signal to actuate the inhaler to achieve the desired interval of inhaler actuation. In some embodiments, the cue signal is communicated directly to the patient and the cue signal includes an audio cue, a visual due, a haptic cue, etc., or combinations thereof. For example, in some embodiments, the cue is visual via activating a green light on the computing device that signals the patient to actuate the inhaler. In other embodiments, the cue signal is electronically communicated (e.g., via wires or wireless communication protocols) to an actuation mechanism of the inhaler to automatically actuate the inhaler to achieve the desired interval of inhaler actuation. For example, in some embodiments the actuation mechanism includes a pressing device secured to the body of the inhaler and is configured to depress a pressurized cannister inside the inhaler to actuate medication delivery. The pressing device can be driven by any mechanical pressing means used in the art, such as a servo motor, hydraulic pump, pneumatic pump, etc. The actuation mechanism includes a microcontroller configured to receive the cue signal wirelessly (via e.g., Bluetooth, Wi-Fi, etc.) and activate the pressing device. In some embodiments, the computing device is integrally formed with the inhaler for directly communicating the cue signal to the actuation mechanism.

At 260, the method 200 includes obtaining inhaler actuation data based on the patient's actuation of the inhaler. In some embodiments, the inhaler actuation data is obtained via the sensor discussed above. In some embodiments, the inhaler actuation data is obtained via an additional sensor, which may be any one or any combination of the types of sensors discussed above. At 270, the computing device receives the inhaler actuation data and, at 280, performs an actuation analysis algorithm on the inhaler actuation data to determine whether the patient achieved the desired interval of inhaler actuation. At 290, the method 200 includes adjusting the cue to the patient to actuate the inhaler to achieve the desired interval for a future actuation. For example, if the patient received a visual cue and failed to achieve the desired interval, then the system can adjust the cue for the next actuation to include an audio cue.

Figure 5:
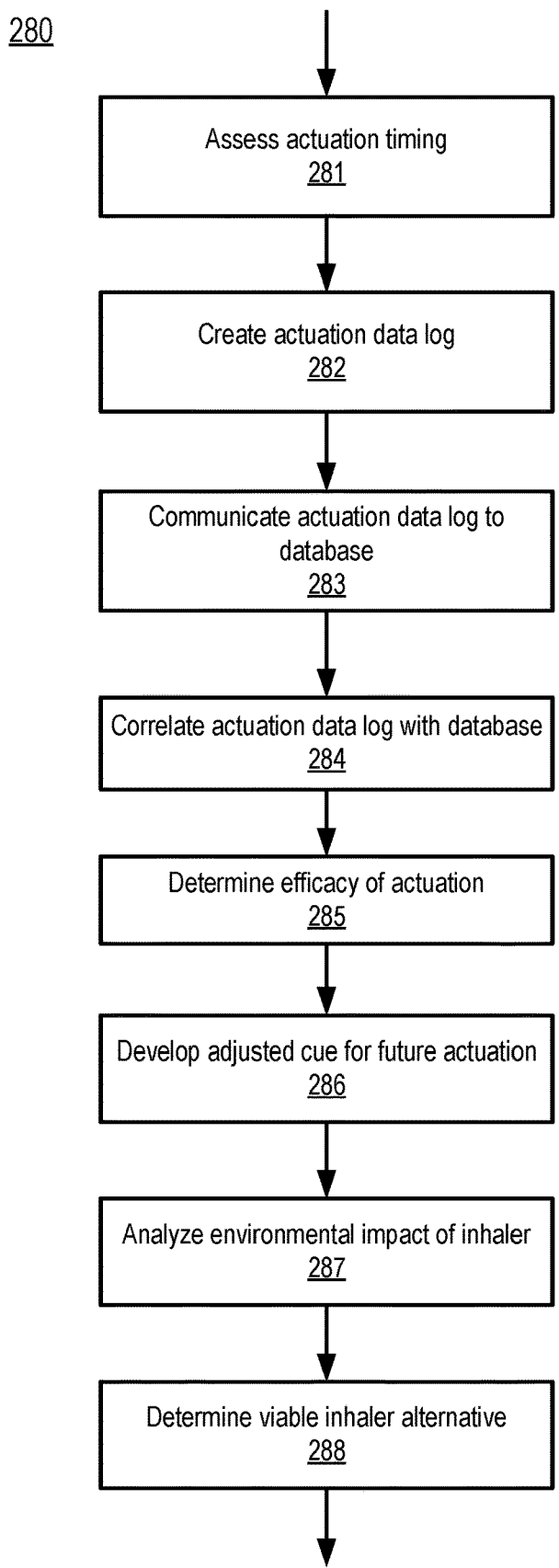
FIG. 5 is a flowchart further outlining the actuation analysis algorithm of the method of FIG. 2.

FIG. 5 illustrates a flowchart of the step 280 of performing the actuation analysis algorithm according to some embodiments of the present technology. In some embodiments, the actuation analysis algorithm is configured for monitoring and providing feedback regarding the efficacy of the medication delivery. At 281, the actuation analysis algorithm determines if the inhaler was actuated at the desired interval by assessing the actuation timing. The actuation analysis algorithm is configured to confirm that medication delivery occurred at the appropriate time (i.e., whether the desired interval was achieved). At 282, the actuation analysis algorithm is configured to create an actuation instance data log of the inhaler actuation data and the timing information. At 283, the actuation instance data log is communicated to a storage, such as database 130. The actuation instance data log can be stored on the computing device and/or communicated to a remote computing device for local and/or remote storage and monitoring. For example, in some embodiments the actuation analysis algorithm confirms that medication delivery occurred at the appropriate time by monitoring, via the sensor, the patient for a brief, rapid burst in flow toward the patient, which the algorithm records as an actuation of the inhaler. In some embodiments, if such a rapid burst in flow is detected after the cue is provided to the patient (or after the actuation signal is communicated to the inhaler), then the algorithm records the actuation instance as a successful medication delivery.

At 284, the actuation analysis algorithm is configured to correlate the actuation instance data log with additional data stored on the database, such as historical data of the patient, historical data of similarly diagnosed patients using the same type of inhaler as the patient, etc. The actuation analysis algorithm correlates the actuation instance data log with the additional data to track and monitor symptoms, side-effects, and/or exacerbations of the patient's underlying pathological condition that is being treated by the inhaler-delivered medication. For example, in some embodiments, the actuation analysis algorithm is configured for correlation and tracking regarding the patient's symptoms and any exacerbation of the symptoms. In some embodiments, the actuation analysis algorithm is configured to monitor the patient for side effects, such as coughing, or potential ineffective medication delivery, such as the patient failing to correctly actuate the inhaler. In some embodiments, the actuation analysis algorithm is configured to compare the patient's records with other patients' records and propose alternative therapies that may be better tolerated by the patient and/or result in more effective medication delivery.

At 285, the actuation analysis algorithm is configured to determine the efficacy of the inhaler actuation. In some embodiments, the efficacy of the inhaler actuation is determined by analyzing the inhaler actuation data and assessing if the amount or percentage of the medication dose effectively received by the patient meets a predetermined threshold (also referred to herein as a success threshold). For example, in some embodiments the algorithm considers a successful actuation to mean that at least 95% of the medication dose was effectively received by the patient. In some embodiments, the algorithm considers a successful actuation to mean that at least 90% of the medication dose was effectively received by the patient. At 286, if the actuation analysis algorithm determined that the inhaler actuation was ineffective (i.e., the dose received by the patient was below the success threshold), the actuation analysis algorithm develops an adjusted cue signal for the next actuation, as described above.

In some embodiments, the actuation analysis algorithm includes continuous respiratory monitoring wherein the system is configured to continuously monitor the patient's respiratory patterns using the sensor to track metrics such as inhalation speed, volume, and depth, and the frequency and regularity of breaths. By such continuous monitoring, the system assesses the effectiveness of the medication delivery and identifies any changes in the patient's respiratory patterns.

In some embodiments, the actuation analysis algorithm includes medication adherence tracking wherein the system is configured to track the patient's medication adherence by recording the timing and frequency of inhaler actuations. The algorithm compares the patient's actual medication usage with the prescribed regimen and calculates adherence metrics, such as the percentage of doses taken on time, times when the patient does not use the medication correctly, and when the patient appears to be using the medication extra times which may suggest poor disease control.

In some embodiments, the actuation analysis algorithm includes user feedback wherein the system permits the patient to provide feedback on the effectiveness of the medication, any side effects experienced, and their overall satisfaction with the inhaler and therapeutic regimen. In some embodiments, the actuation analysis algorithm includes clinical outcome monitoring wherein the system is configured to monitor clinical outcomes, such as symptom relief and/or improvement, pulmonary function changes, and quality of life measures. The algorithm tracks (e.g., by storing data in a database for future use and cross-reference with other data) data regarding patient responses to questionaries, patient-reported outcome measures, and objective tests such as spirometry or peak flow measurements.

In some embodiments, the actuation analysis algorithm includes alerts and notifications wherein the system is configured to generate alerts and notifications based on the patient's respiratory patterns, medication adherence, and clinical outcomes. These alerts may be sent to the patient, healthcare providers, or caregivers, depending on the patient's preferences. In some embodiments, the alerts provide recommendations for actions to take, such as adjusting the medication dosage, adding additional controller medications (e.g., allergy medicine, nasal sprays, oral medications such as antibiotics) or seeking medical attention. In some embodiments, the actuation analysis algorithm includes reports and dashboards wherein the system is configured to provide reports and dashboards that summarize the patient's respiratory patterns, medication adherence, and clinical outcomes. These reports may be accessible to the patient, healthcare providers, and caregivers, and provide a comprehensive view of the patient's respiratory health and treatment progress. In some embodiments, the above alerts, notifications, reports, and dashboards are provided to the patient via a display of the computing device or communicated to the patient's personal computing device such as a Smartphone. In some embodiments, the above alerts, notifications, reports, and dashboards are provided to healthcare provides and/or caregivers via a display of the computing device or communicated via a network to a remote server or computing device.

In some embodiments, the actuation analysis algorithm includes data sharing wherein the system permits the patient to share their data (e.g., via network communication to a remote server or computing device) with healthcare providers, caregivers, researchers, or other stakeholders. This data sharing facilitates collaboration and coordination among the patient's care team and supports evidence-based decision-making. In some embodiments, the actuation analysis algorithm includes telemedicine integration wherein the system is configured to integrate with telemedicine platforms (e.g., via wired or wireless network connections), permitting the patient to have virtual consultations with their healthcare providers. During such consultations, the healthcare provider may review the patient's respiratory patterns, medication adherence, and clinical outcomes, and adjust the treatment plan as needed.

In some embodiments, at 287, the actuation analysis algorithm includes environmental initiatives wherein the system is configured to access a database containing data regarding the environmental impact of all FDA approved inhalers. The algorithm cross-references data on the environmental impact of the patient's current inhaler with the environmental impact data of other available inhalers and, at 288, determines if a more environmentally friendly inhaler is available for use that still meets the patient's treatment regimen. If so, the algorithm recommends the patient switch to a different inhaler type. For example, the algorithm can recommend an inhaler that minimizes or avoids use of a propellant that is considered a greenhouse gas or is otherwise damaging.

Accordingly, embodiments of the present technology are configured to monitor and predict a patient's respiratory cycle to optimize medication delivery, whereas prior art inhaler coaching techniques and devices are limited to training the patient to inhale at the correct speed. Embodiments of the present technology are configured for use with any type of inhaler, whereas prior art inhaler coaching techniques and devices are specifically designed for use with pressurized metered dose inhalers ("pMDIs"). Embodiments of the present technology are configured to be implemented in a software application of any type of computing device that uses sensors to monitor the patient's breathing, whereas prior art inhaler coaching techniques and devices are limited to implementation as physical inhaler devices. Additionally, prior art inhaler coaching techniques and devices fail because they require the patient and/or healthcare provider to perform actions beyond the capability of the human mind, such as the ability to accurately and precisely detect breath patterns, control breath speed and timing, synchronize actuation cues with the breath patterns, monitor and analyze medication dose results, etc. Thus, the present technology improves computer functionality and respiratory medication delivery.

Some embodiments of the present technology assist patients in avoiding common inhaler use errors such as: incorrect inhaler preparation, failure to remove protective cap, proper body posture, proper inhaler positioning during preparation and inhalation, exhalation completely before inhalation, failure to seal teeth and lips around mouthpiece, not having an empty mouth before inhalation, actuation of the inhaler at incorrect time relative to breathing in, failing to hold breath for sufficient time, not breathing out calmly after inhalation, and not rinsing mouth. Many of these errors are addressed by prompts from the system to the user.

As will be appreciated by those of skill in the art, embodiments of the present technology can improve health outcomes, some of which can be measured with the clinical COPD Questionnaire ("CCQ") or the COPD Assessment Test ("CAT").

As will be apparent to those skilled in the art, various modifications, adaptations, and variations of the foregoing specific disclosure can be made without departing from the scope of the technology claimed herein. The various features and elements of the technology described herein may be combined in a manner different than the specific examples described or claimed herein without departing from the scope of the technology. In other words, any element or feature may be combined with any other element or feature in different embodiments, unless there is an obvious or inherent incompatibility between the two, or it is specifically excluded.

References in the specification to "one embodiment," "an embodiment," etc., indicate that the embodiment described may include a particular aspect, feature, structure, or characteristic, but not every embodiment necessarily includes that aspect, feature, structure, or characteristic. Moreover, such phrases may, but do not necessarily, refer to the same embodiment referred to in other portions of the specification. Further, when a particular aspect, feature, structure, or characteristic is described in connection with an embodiment, it is within the knowledge of one skilled in the art to affect or connect such aspect, feature, structure, or characteristic with other embodiments, whether or not explicitly described.

The singular forms "a," "an," and "the" include plural reference unless the context clearly dictates otherwise. Thus, for example, a reference to "a plant" includes a plurality of such plants. It is further noted that the claims may be drafted to exclude any optional element. As such, this statement is intended to serve as antecedent basis for the use of exclusive terminology, such as "solely," "only," and the like, in connection with the recitation of claim elements or use of a "negative" limitation. The terms "preferably," "preferred," "prefer," "optionally," "may," and similar terms are used to indicate that an item, condition, or step being referred to is an optional (not required) feature of the technology.

The term "and/or" means any one of the items, any combination of the items, or all of the items with which this term is associated. The phrase "one or more" is readily understood by one of skill in the art, particularly when read in context of its usage.

Each numerical or measured value in this specification is modified by the term "about." The term "about" can refer to a variation of ±5%, ±10%, ±20%, or ±25% of the value specified. For example, "about 50" percent can in some embodiments carry a variation from 45 to 55 percent. For integer ranges, the term "about" can include one or two integers greater than and/or less than a recited integer at each end of the range. Unless indicated otherwise herein, the term "about" is intended to include values and ranges proximate to the recited range that are equivalent in terms of the functionality of the composition, or the embodiment.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. A recited range (e.g., weight percents of carbon groups) includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third, and upper third, etc.

As will also be understood by one skilled in the art, all language such as "up to," "at least," "greater than," "less than," "more than," "or more," and the like, include the number recited and such terms refer to ranges that can be subsequently broken down into sub-ranges as discussed above. In the same manner, all ratios recited herein also include all sub-ratios falling within the broader ratio. Accordingly, specific values recited for radicals, substituents, and ranges, are for illustration only; they do not exclude other defined values or other values within defined ranges for radicals and substituents.

One skilled in the art will also readily recognize that where members are grouped together in a common manner, such as in a Markush group, the technology encompasses not only the entire group listed as a whole, but each member of the group individually and all possible subgroups of the main group. Additionally, for all purposes, the technology encompasses not only the main group, but also the main group absent one or more of the group members. The technology therefore envisages the explicit exclusion of any one or more of members of a recited group. Accordingly, provisos may apply to any of the disclosed categories or embodiments whereby any one or more of the recited elements, species, or embodiments, may be excluded from such categories or embodiments, for example, as used in an explicit negative limitation.

What is claimed is:

1. A method of coaching a patient to use an inhaler for medication delivery, the method comprising:
    obtaining, via a sensor, respiratory behavior data of the patient;
    receiving, at a computing device, the respiratory behavior data;
    performing a respiratory pattern analysis algorithm on the respiratory behavior data to determine a desired interval of inhaler actuation for medication delivery;
    communicating a cue signal to actuate the inhaler to achieve the desired interval of inhaler actuation;
    obtaining, via the sensor, inhaler actuation data based on the actuation of the inhaler;
    receiving, at the computing device, the inhaler actuation data;
    performing an actuation analysis algorithm on the inhaler actuation data to assess the efficacy of the actuation; and
    adjusting, if the efficacy of the actuation is below a predetermined threshold, the cue signal to actuate the inhaler to improve the efficacy of a future actuation.

2. The method of claim 1, wherein performing the respiratory pattern analysis algorithm comprises:
    analyzing the respiratory behavior data to determine a current breathing pattern of the patient;
    confirming that the current breathing pattern is predictable within a predetermined margin of error;
    confirming that the current breathing pattern is compatible with medication delivery via actuation of the inhaler; and synchronizing the current breathing pattern with the actuation of the inhaler to determine the desired interval of inhaler actuation.

3. The method of claim 2, further comprising:
communicating a sample cue signal to the patient to perform a pseudo actuation of the inhaler;
obtaining, via the sensor, sample inhalation data of the patient;
receiving, at the computing device, the sample inhalation data; and
performing the respiratory pattern analysis algorithm on the sample inhalation data.

4. The method of claim 1, wherein performing the actuation analysis algorithm comprises:
determining if the inhaler was actuated at the desired interval;
creating an actuation instance data log based, at least in part, on the inhaler actuation data;
communicating the actuation instance data log to a database;
correlating the actuation instance data log with historical data of the patient and historical data of similarly diagnosed patients stored on the database to track and monitor symptoms, side-effects, and exacerbations of a pathological condition of the patient being treated by the inhaler-delivered medication;
determining the efficacy of the actuation based, at least in part, on the correlated actuation instance data log; and
developing an adjusted cue signal to improve the efficacy of a future actuation.

5. The method of claim 4, wherein performing the actuation analysis algorithm further comprises:
analyzing the environmental impact of the inhaler; and
determining whether an alternative inhaler having a more beneficial environmental impact than the environmental impact of the inhaler is available for use with the patient's medication.

6. The method of claim 1, wherein the cue signal is communicated to the patient and the cue signal comprises an audio cue, a visual due, a haptic cue, or combinations thereof.

7. The method of claim 1, wherein the cue signal is communicated to an actuation mechanism of the inhaler that is configured to automatically actuate the inhaler upon receiving the cue signal.

8. A system for coaching a patient to use an inhaler for medication delivery, the system comprising:
an inhaler configured to deliver medication prescribed to a patient;
a sensor configured to obtain respiratory behavior data of the patient; and
a computing device configured to receive the respiratory behavior data, the computing device comprising inhaler coaching circuitry and a memory configured to execute instructions of the inhaler coaching circuitry via at least one processor, the instructions comprising:
obtaining, via the sensor, respiratory behavior data of the patient;
receiving, at the computing device, the respiratory behavior data;
performing a respiratory pattern analysis algorithm on the respiratory behavior data to determine a desired interval of inhaler actuation for medication delivery;
communicating a cue signal to actuate the inhaler to achieve the desired interval of inhaler actuation;
obtaining, via the sensor, inhaler actuation data based on the actuation of the inhaler;
receiving, at the computing device, the inhaler actuation data;
performing an actuation analysis algorithm on the inhaler actuation data to assess the efficacy of the actuation; and
adjusting, if the efficacy of the actuation is below a predetermined threshold, the cue signal to actuate the inhaler to improve the efficacy of a future actuation.

9. The system of claim 8, wherein performing the respiratory pattern analysis algorithm comprises:
analyzing the respiratory behavior data to determine a current breathing pattern of the patient;
confirming that the current breathing pattern is predictable within a predetermined margin of error;
confirming that the current breathing pattern is compatible with medication delivery via actuation of the inhaler; and
synchronizing the current breathing pattern with the actuation of the inhaler to determine the desired interval of inhaler actuation.

10. The system of claim 9, wherein the instructions of the inhaler coaching circuitry executed by the memory via the at least one processor further comprise:
communicating a sample cue signal to the patient to perform a pseudo actuation of the inhaler;
obtaining, via the sensor, sample inhalation data of the patient;
receiving, at the computing device, the sample inhalation data; and
performing the respiratory pattern analysis algorithm on the sample inhalation data.

11. The system of claim 8, wherein performing the actuation analysis algorithm comprises:
determining if the inhaler was actuated at the desired interval;
creating an actuation instance data log based, at least in part, on the inhaler actuation data;
communicating the actuation instance data log to a database;
correlating the actuation instance data log with historical data of the patient and historical data of similarly diagnosed patients stored on the database to track and monitor symptoms, side-effects, and exacerbations of a pathological condition of the patient being treated by the inhaler-delivered medication;
determining the efficacy of the actuation based, at least in part, on the correlated actuation instance data log; and
developing an adjusted cue signal to improve the efficacy of a future actuation.

12. The system of claim 11, wherein the database further includes environmental impact data regarding the inhaler and a plurality of alternative inhalers; and
wherein performing the actuation analysis algorithm further comprises:
analyzing the environmental impact of the inhaler; and
determining whether an alternative inhaler having a more beneficial environmental impact than the environmental impact of the inhaler is available for use with the patient's medication.

13. The system of claim 8, wherein the cue signal is communicated to the patient and the cue signal comprises an audio cue, a visual due, a haptic cue, or combinations thereof.

14. The system of claim 8, wherein the cue signal is communicated to an actuation mechanism of the inhaler that is configured to automatically actuate the inhaler upon receiving the cue signal.

15. A non-transitory computer readable medium comprising instructions that, when executed by at least one processor, coach a patient to use an inhaler for medication delivery, the instructions comprising:

obtaining, via a sensor, respiratory behavior data of a patient;
receiving, at a computing device, the respiratory behavior data;
performing a respiratory pattern analysis algorithm on the respiratory behavior data to determine a desired interval of inhaler actuation for medication delivery;
communicating a cue signal to actuate the inhaler to achieve the desired interval of inhaler actuation;
obtaining, via the sensor, inhaler actuation data based on the actuation of the inhaler;
receiving, at the computing device, the inhaler actuation data;
performing an actuation analysis algorithm on the inhaler actuation data to assess the efficacy of the actuation; and
adjusting, if the efficacy of the actuation is below a predetermined threshold, the cue signal to actuate the inhaler to improve the efficacy of a future actuation.

16. The non-transitory computer readable medium of claim 15, wherein performing the respiratory pattern analysis algorithm comprises:

analyzing the respiratory behavior data to determine a current breathing pattern of the patient;
confirming that the current breathing pattern is predictable within a predetermined margin of error;
confirming that the current breathing pattern is compatible with medication delivery via actuation of the inhaler; and
synchronizing the current breathing pattern with the actuation of the inhaler to determine the desired interval of inhaler actuation.

17. The non-transitory computer readable medium of claim 16, further comprising:

communicating a sample cue signal to the patient to perform a pseudo actuation of the inhaler;
obtaining, via the sensor, sample inhalation data of the patient;
receiving, at the computing device, the sample inhalation data; and
performing the respiratory pattern analysis algorithm on the sample inhalation data.

18. The non-transitory computer readable medium of claim 15, wherein performing the actuation analysis algorithm comprises:

determining if the inhaler was actuated at the desired interval;
creating an actuation instance data log based, at least in part, on the inhaler actuation data;
communicating the actuation instance data log to a database;
correlating the actuation instance data log with historical data of the patient and historical data of similarly diagnosed patients stored on the database to track and monitor symptoms, side-effects, and exacerbations of a pathological condition of the patient being treated by the inhaler-delivered medication;
determining the efficacy of the actuation based, at least in part, on the correlated actuation instance data log; and
developing an adjusted cue signal to improve the efficacy of a future actuation.

19. The non-transitory computer readable medium of claim 15, wherein the cue signal is communicated to the patient and the cue signal comprises an audio cue, a visual due, a haptic cue, or combinations thereof.

20. The non-transitory computer readable medium of claim 15, wherein the cue signal is communicated to an actuation mechanism of the inhaler that is configured to automatically actuate the inhaler upon receiving the cue signal.

* * * * *